United States Patent [19]
Imaki et al.

[11] Patent Number: 4,968,816
[45] Date of Patent: Nov. 6, 1990

[54] 3,4-DIHYDROXYTETRAHYDROFURAN CARBONATE

[75] Inventors: Naoshi Imaki, Atsugi; Isao Kawakami, Machida, both of Japan

[73] Assignee: Mitsubishi Kasei Corporation, Japan

[21] Appl. No.: 312,034

[22] Filed: Feb. 16, 1989

[30] Foreign Application Priority Data

Sep. 1, 1987 [JP] Japan .................. 62-216533

[51] Int. Cl.$^5$ .......................... C07D 493/04
[52] U.S. Cl. .................................. 549/229
[58] Field of Search .................. 549/229, 230

[56] References Cited

U.S. PATENT DOCUMENTS 2,446,145  7/1948  Strain ................................... 549/229
2,522,680  9/1950  Krupa et al. ......................... 549/229

Primary Examiner—Richard L. Raymond
Assistant Examiner—Mark W. Russell
Attorney, Agent, or Firm—Jordan B. Bierman

[57] ABSTRACT 3,4-Dihydroxytetrahydrofuran carbonate of the structural formula:

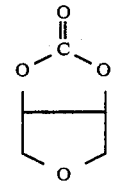

and a Process for the Production thereof.

1 Claim, No Drawings

3,4-DIHYDROXYTETRAHYDROFURAN CARBONATE

BACKGROUND OF THE INVENTION

1. Field of the invention

The present invention relates to 3, 4-dihydroxytetrahydrofuran carbonate and a process for the production thereof.

The 3, 4-dihydroxytetrahydrofuran carbonate of the present invention is a novel compound, and is expected to find applications as a starting material for dielectric materials in fields of condensers, batteries, etc., as a starting material for organic fine chemicals, as an intermediate for medicines, etc. and the like.

2. Description of the Prior art

Of oxygen-containing organic compounds, γ-butyllactone and propylene carbonate have been known as compounds having high dielectric constants. However, although these compounds exhibit relatively high dielectric constants, their dielectric constants were not fully satisfactory.

SUMMARY OF THE INVENTION

The present invention aims to provide an oxygen-containing organic compound having a dielectric constant higher than those of γ-butyllactone and propylene carbonate.

The present inventors have been intensively studying in order to solve the above-described problem and, as a result, have succeeded in development of 3, 4-dihydroxytetrahydrofuran carbonate which is a novel compound exhibiting an extremely high dielectric constant and a process for the production thereof.

In other words, the 3, 4-dihydroxytetrahydrofuran carbonate of the present invention is a compound represented by the structural formula:

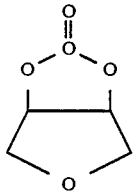

Further, the process for the production of 3, 4-dihydroxytetrahydrofuran carbonate of the present invention is a process which is characterized by reacting phosgene or a haloformic acid alkyl ester on 3, 4-dihydroxytetrahydrofuran or an alkali metal salt thereof.

DETAILED DESCRIPTION OF THE PREFERRED EMBODIMENTS

To describe in detail the process for the production of 3, 4-dihydroxytetrahydrofuran carbonate of the present invention, the starting material therefor may be either 3, 4-dihydroxytetrahydrofuran (which may also be referred to as "erythritan") or an alkali metal salt thereof such as of Na, K, Li, etc. Its alkali metal salt may easily be obtained by reacting an alkali metal or an alkali metal hydride on 3, 4-dihydroxytetrahydrofuran.

The reaction for the production of the present invention is preferably conducted by dissolving 3, 4-dihydroxytetrahydrofuran or an alkali metal salt thereof in an inert solvent. As the inert solvent, there may be mentioned, in the case of 3, 4-dihydroxytetrahydrofuran, for example, tetrahydrofuran, dioxane, diethyl ether, dimethylsulfoxide, dimethylformamide, dichloroethane, methylene chloride, etc. Further, as the inert solvent in the case of an alkali metal salt of 3, 4-dihydroxytetrahydrofuran, there may be used solvents stable against alkali metals such as tetrahydrofuran, dioxane, diethyl ether, dimethylformamide, N-methyl-2-pyrrolidone, etc. The amount of such inert solvents used is 100 times (by weight) or less, preferably 2-20 times (by weight), based on 3, 4-dihydroxytetrahydrofuran or an alkali metal salt thereof. The reaction ratio of 3, 4-dihydroxytetrahydrofuran or an alkali metal salt thereof to phosgene or a haloformic acid alkyl ester is generally such that the latter is generally 0.5–5.0 moles, preferably 0.8–2.0 moles, per mole of the former.

For supplying phosgene to the reaction system, phosgene may be directly supplied in a gaseous state, or phosgene may be supplied in a state dissolved in an inert solvent such as benzene, toluene, etc. Further, in the case of a haloformic acid alkyl ester, it may be directly supplied, or may be supplied by dissolving in an appropriate inert solvent.

As said haloformic acid alkyl ester, there may be mentioned, for example, chloroformic acid alkyl esters, bromoformic acid alkyl esters, fluoroformic acid alkyl esters, etc. of which chloroformic acid alkyl esters are preferred. Further, as the alkyl in said haloformic acid alkyl ester, there may be mentioned methyl, ethyl, butyl, octyl, etc. of which methyl and ethyl are preferred.

To said reaction system, a base such as pyridine, a tertiary alkylamine (e. g. trimethylamine, triethylamine, etc.) may be added as a catalyst The amount of said catalyst is 10 times (by weight) or less, more preferably 1.8-3 times (by weight) in the molar ratio to 3, 4-dihydroxytetrahydrofuran.

The reaction temperature therefor is a temperature from −78° C. to the boiling point of the solvent used, preferably between −30° C. and 30° C. If the reaction temperature is too high, it is not preferred because it causes polymerization. The reaction time varies depending on the reaction temperature or the presence or absence of the catalyst, but in general, it is within the range of one minute to 2 days, preferably an hour to 24 hours, after the addition of phosgene or a haloformic acid alkyl ester.

After the reaction, where the catalyst has not been added, the intended 3, 4-dihydroxytetrahydrofuran carbonate may be obtained by distilling off the solvent, or where the catalyst has been added, the intended carbonate may be obtained by filtering off the precipitate and thereafter distilling off the solvent.

The present invention is described in mode detail by the following example and experiment example.

EXAMPLE 1

To a solution obtained by dissolving 5.20 g (0.050 mole) of 3, 4-dihydroxytetrahydrofuran (hereinafter referred to as "erythritan") in 30 ml of tetrahydrofuran was added to a mixed solution of 50 ml of a toluene solution containing 20% by weight of phosgene dissolved in toluene and 20 ml of tetrahydrofuran. Said mixture was cooled to ca.0° C. with ice water, and 50 ml of pyridine was added dropwise After its addition, the reaction system was allowed to become room temperature, the precipitate was removed by filtration and thereafter the solvent was distilled off. Further, for purification, the product was dissolved by adding water, extracted with chloroform, and the chloroform was distilled off the extract to obtain the intended 3,4-dihydroxytetrahydrofuran carbonate.

Its yield was 3.80 g, the melting point was 65°-70° C., and the elemental analytical values were as follows against the calculated values.

|  | Carbon | Hydrogen | Oxygen |
|---|---|---|---|
| Calculated Value (%) | 46.16 | 4.65 | 49.19 |
| Analytical Value (%) | 46.19 | 4.71 | 49.10 |

The results of its H-NMR analysis were as follows:

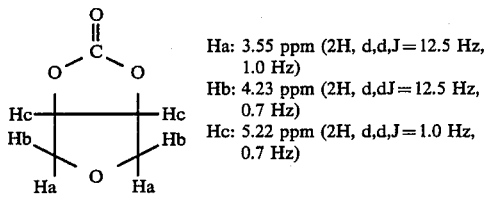

Ha: 3.55 ppm (2H, d,d,J=12.5 Hz, 1.0 Hz)
Hb: 4.23 ppm (2H, d,dJ=12.5 Hz, 0.7 Hz)
Hc: 5.22 ppm (2H, d,d,J=1.0 Hz, 0.7 Hz)

EXPERIMENT EXAMPLE 0.8 M Solutions of 3, 4-dihydroxytetrahydrofuran carbonate, γ-butyllactone and propylene carbonate in dioxane respectively and neat dioxane were measured for the specific inductive capacity respectively. The results are shown in Table 1.

TABLE 1

| Sample | Specific Inductive Capacity (100 kHz) |
|---|---|
| Dioxane (Blank test) | 2.26 |
| 0.08M Solution of 3, 4-dihydroxytetrahydrofuran carbonate in dioxane | 5.32 |
| 0.8M Solution of γ-butyllactone in dioxane | 3.90 |
| 0.8M Solution of propylene carbonate in dioxane | 4.82 |

Notes for Table 1:
The conditions for measurement were as follows: Equipment used: YHP. Automatic Capacitance Bridge 4270 A Cell: Dielectric cells for liquids Temperature and humidity for measurement: 23° C., 50% RH

EXAMPLE 2

10.4 g (0.1 mole) of erythritan was dissolved in 100 ml of chloroform. 5.43 g (0.05 mole) of ethyl chloroformate was added thereto, then cooled to 5° C. with ice-water, 7.9 g, (0.1 mole) of pyridine was added and thereafter the reaction was effected by heating at reflux at normal pressure for 6 hours.

The reaction mixture was filtered, and the chloroform was distilled off. Further, the product was dissolved by adding water, then extracted with chloroform, and thereafter the chloroform was distilled off from the extract to obtain 5.2 g of 3, 4-dihydroxytetrahydrofuran carbonate.

EXAMPLE 3

1.04 g (0.01 mole) of erythritan was dissolved in 10 ml of tetrahydrofuran, 20 ml of a toluene solution containing 20% by weight of phosgene was added thereto, and the reaction was effected with ice-cooling for 6 hours. After the reaction, 3 ml of triethylamine was added, the formed precipitate was removed by filtration, and thereafter the toluene, tetrahydrofuran and triethylamine were distilled off. Further, the product was dissolved by adding water, extracted with chloroform, and the chloroform was distilled off from the extract to obtain 0.66 g of 3,4-dihydroxytetrahydrofuran carbonate.

The 3,4-dihydroxytetrahydrofuran carbonate of the present invention is a novel compound having an extremely high dielectric constant.

What is claimed is:
1. 3,4-Dihydroxytetrahydrofuran carbonate of the structural formula:

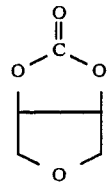

* * * * *